United States Patent
Ozeryansky

(10) Patent No.: US 7,045,069 B2
(45) Date of Patent: May 16, 2006

(54) MICROFABRICATION METHOD BASED ON METAL MATRIX COMPOSITE TECHNOLOGY

(76) Inventor: Gennady Ozeryansky, 39 Newbridge Cir., Cheshire, CT (US) 06410

( * ) Notice: Subject to any disclaimer, the term of this patent is extended or adjusted under 35 U.S.C. 154(b) by 144 days.

(21) Appl. No.: 10/702,856

(22) Filed: Nov. 6, 2003

(65) Prior Publication Data
US 2004/0094503 A1 May 20, 2004

Related U.S. Application Data

(60) Provisional application No. 60/425,998, filed on Nov. 14, 2002.

(51) Int. Cl.
*H01L 21/00* (2006.01)
*C23F 1/00* (2006.01)

(52) U.S. Cl. .................. 216/11; 216/2; 216/7; 216/8; 216/9; 430/320; 428/606; 428/611; 428/614

(58) Field of Classification Search ............ 216/2, 216/7–9, 11; 430/320; 428/606, 611, 614
See application file for complete search history.

(56) References Cited

U.S. PATENT DOCUMENTS

| | | | |
|---|---|---|---|
| 2,499,977 A | 3/1950 | Scott | |
| 2,628,417 A | 2/1953 | Peyches | |
| 3,379,000 A | 4/1968 | Webber | |
| 3,506,885 A | 4/1970 | Roberts | |
| 3,625,662 A | 12/1971 | Roberts | |
| 3,868,792 A | 3/1975 | Roberts | |
| 3,964,482 A | 6/1976 | Gerstel | |
| 4,415,635 A * | 11/1983 | Wilsdorf et al. | 428/611 |
| 5,127,149 A | 7/1992 | Ozeryansky | |
| 5,972,523 A * | 10/1999 | Qin et al. | 428/614 |
| 6,050,988 A | 4/2000 | Zuck | |
| 6,083,196 A | 7/2000 | Trautman | |
| 6,219,574 B1 | 4/2001 | Cormier | |
| 6,331,266 B1 | 12/2001 | Powell | |
| 6,334,856 B1 | 1/2002 | Allen | |
| 6,471,903 B1 | 10/2002 | Sherman | |
| 6,533,949 B1 | 3/2003 | Yeshurun | |
| 6,790,372 B1 * | 9/2004 | Roy et al. | 216/10 |
| 2003/0087130 A1 * | 5/2003 | Sugawara | 428/692 |

OTHER PUBLICATIONS

Concise Encyclopedia of Magnetic & Superconducting Materials, 1992 Pergamon Press, pp. 332-338.
Handbook of Metal-forming Processes, by Betzalel Avitzur 1983, John Wiley & Sons, pp. 429-432.
Fundamentals of Microfabrication, by Madou, Mark CRC Press, LLC 1997, pp. 328-335.

* cited by examiner

*Primary Examiner*—Shamim Ahmed

(57) ABSTRACT

A method of fabricating microstructural components, microparts assemblies and microparts is disclosed. The method includes fabricating a unidirectional metal matrix composite made of materials selected to allow precise etching of different structural elements of the given composite without damage to each other. Cutting a composite to form slices or sections. Etching a matrix entirely out will produce wide assortment of microparts. Partial removal of matrix will form an array of microprotrusions protruding from a substrate. Etching out the microprotrusions cores will form hollow microprotrusions. The method of invention is suitable for fabricating of variety of microcomponents. For example: microneedles—a medical microdevice component having micron features, arrays of high strength micropins and micropunches, and precisely controlled unique microstructural surfaces.

14 Claims, 8 Drawing Sheets

Figure 3:
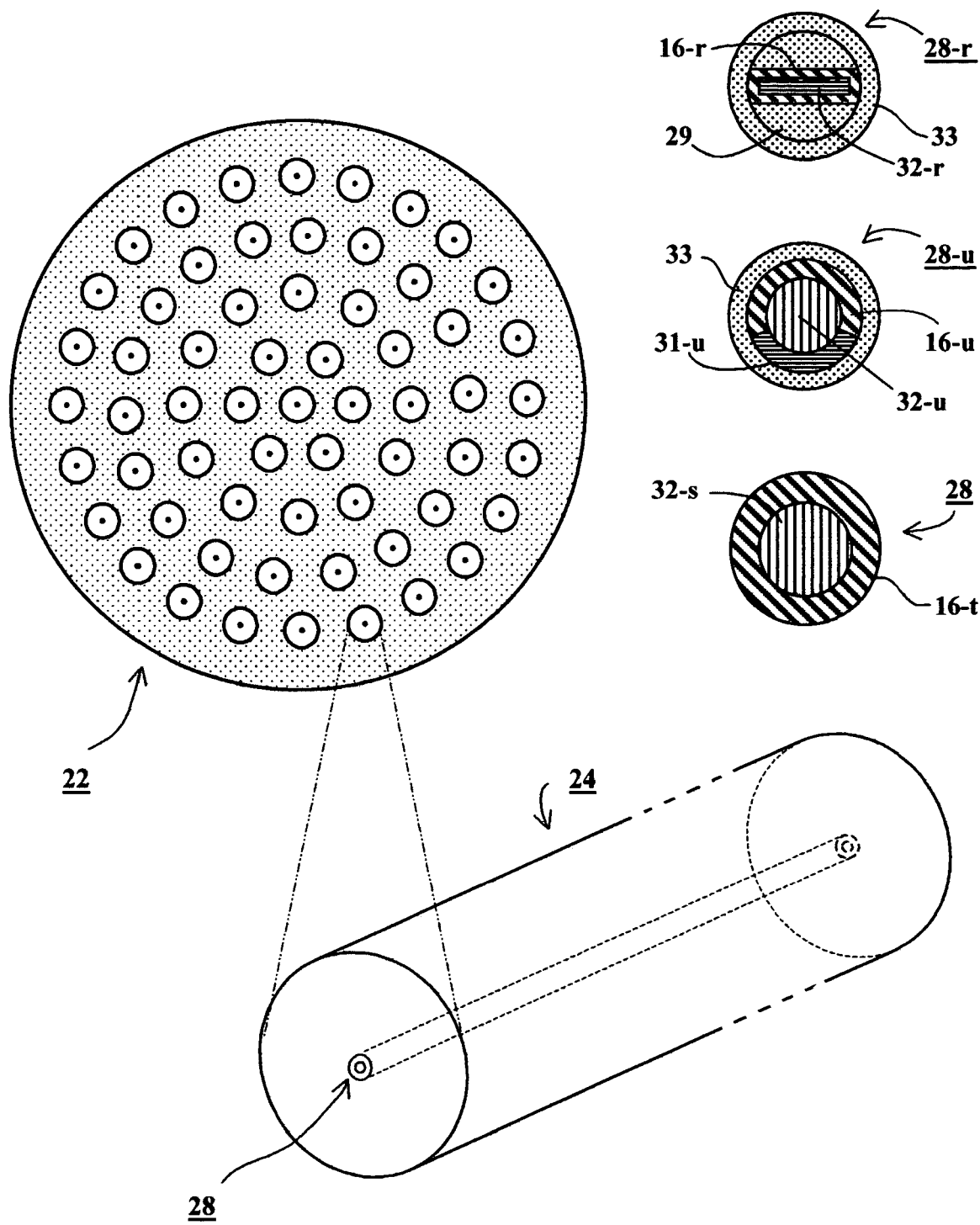

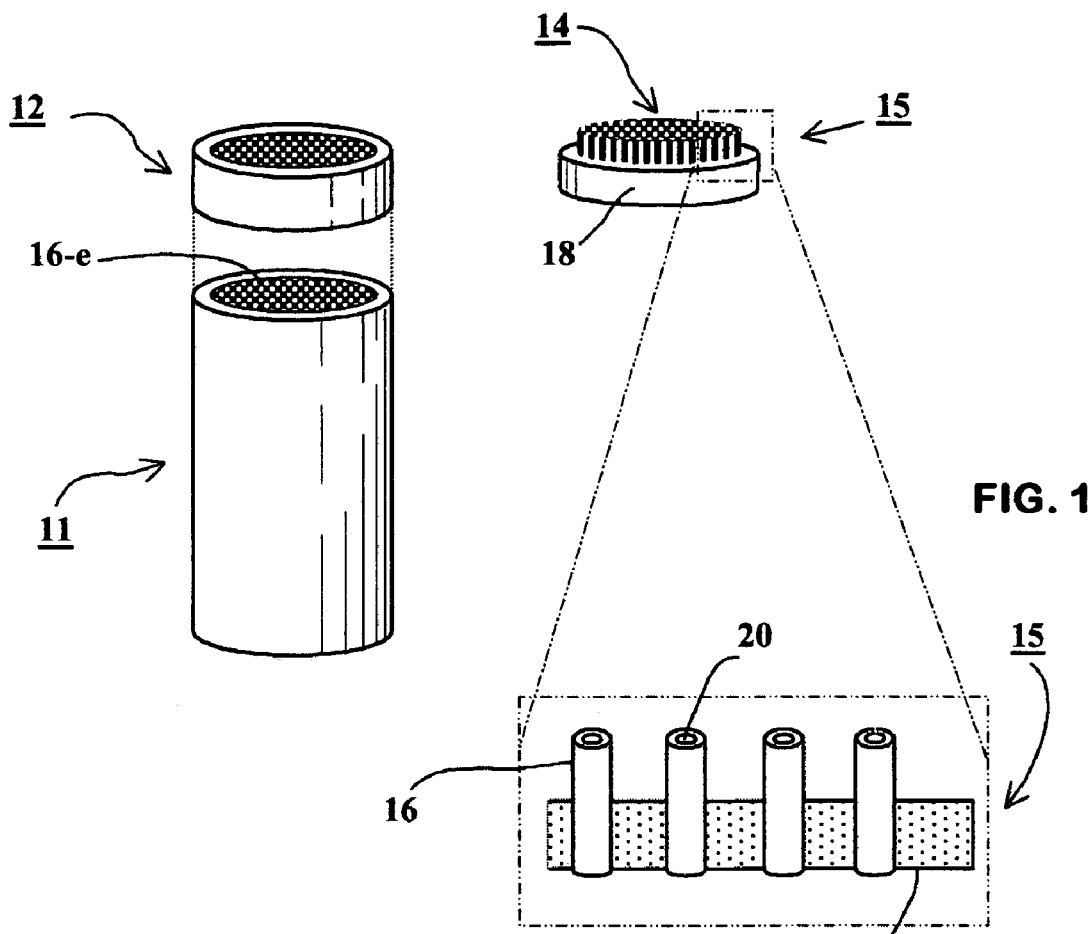
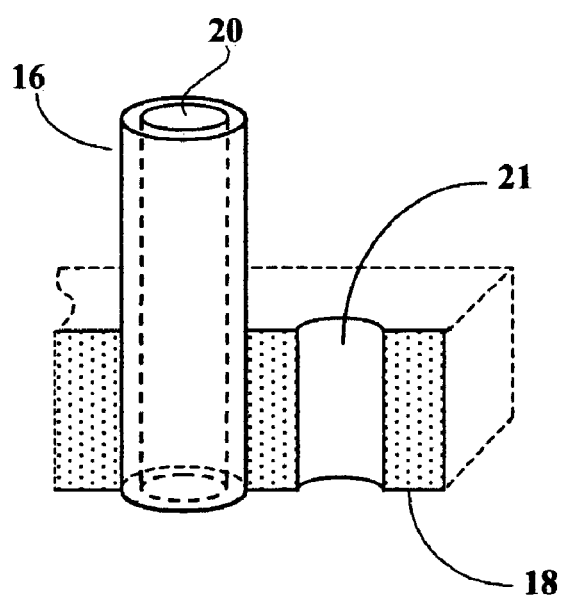
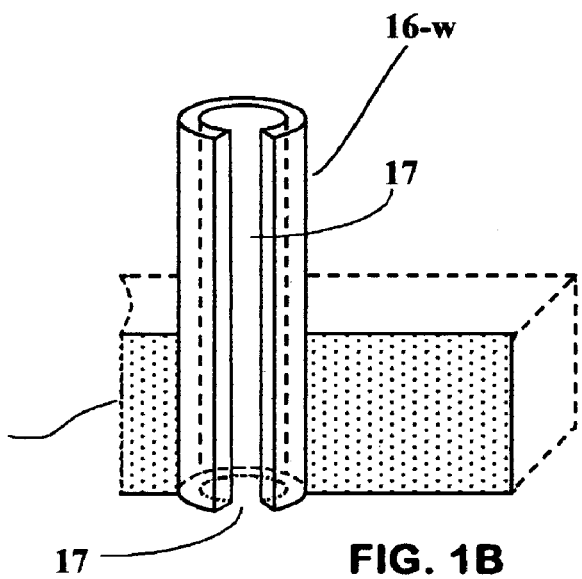
FIG. 1
FIG. 1A
FIG. 1B

FIG. 2

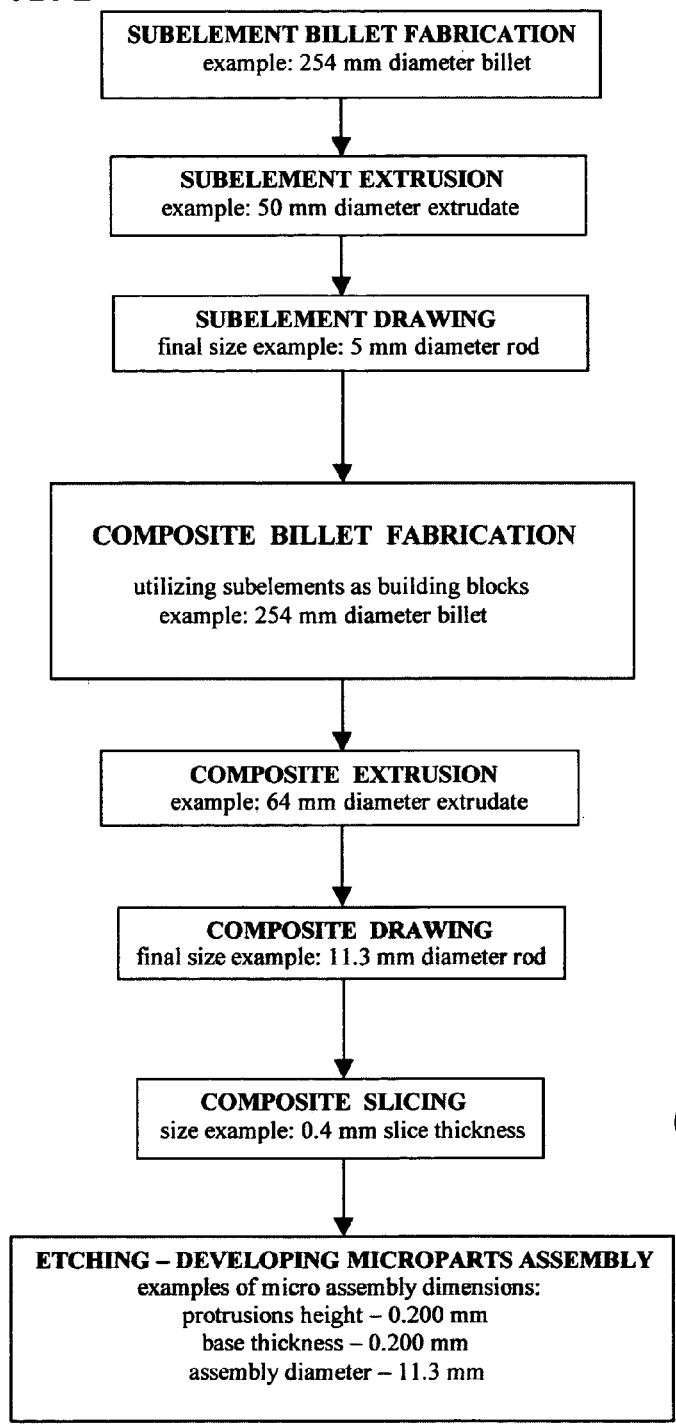
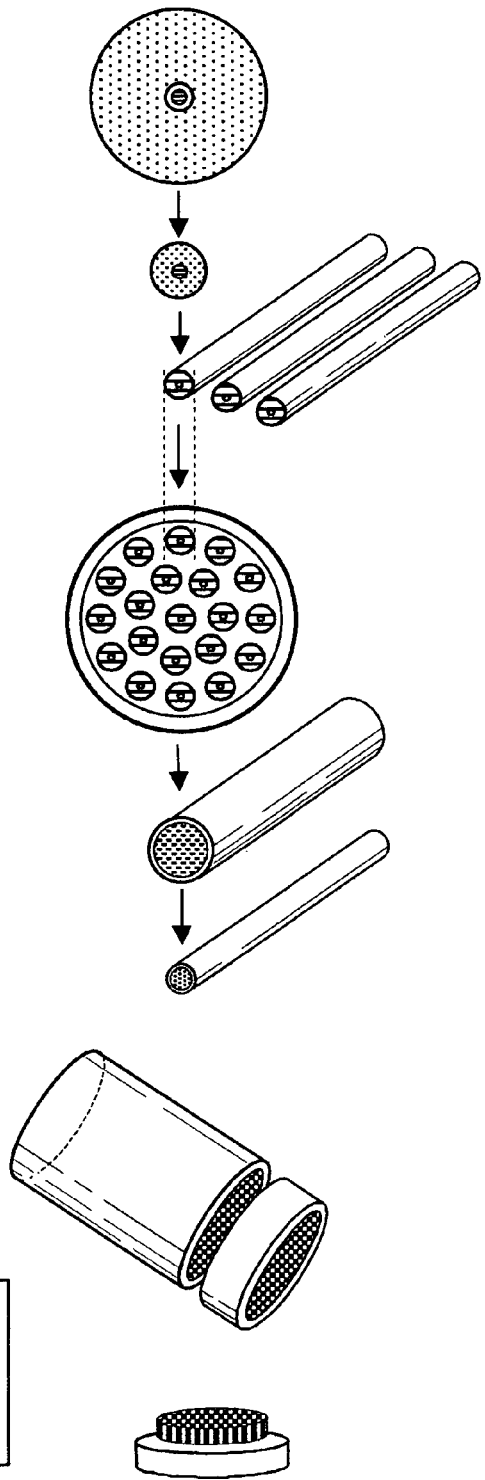

SUBELEMENT BILLET FABRICATION
example: 254 mm diameter billet

↓

SUBELEMENT EXTRUSION
example: 50 mm diameter extrudate

↓

SUBELEMENT DRAWING
final size example: 5 mm diameter rod

↓

COMPOSITE BILLET FABRICATION utilizing subelements as building blocks
example: 254 mm diameter billet

↓

COMPOSITE EXTRUSION
example: 64 mm diameter extrudate

↓

COMPOSITE DRAWING
final size example: 11.3 mm diameter rod

↓

COMPOSITE SLICING
size example: 0.4 mm slice thickness

↓

ETCHING – DEVELOPING MICROPARTS ASSEMBLY
examples of micro assembly dimensions:
protrusions height – 0.200 mm
base thickness – 0.200 mm
assembly diameter – 11.3 mm

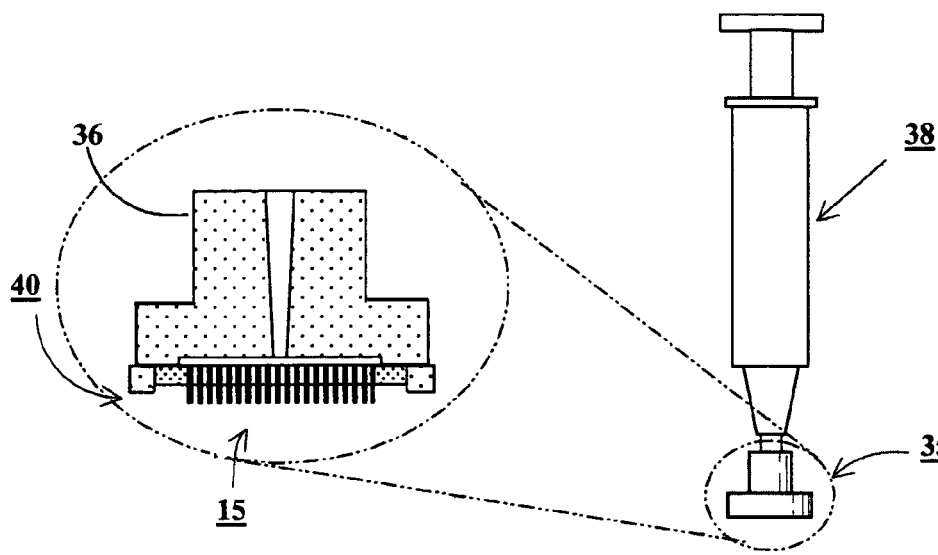
FIG. 8A
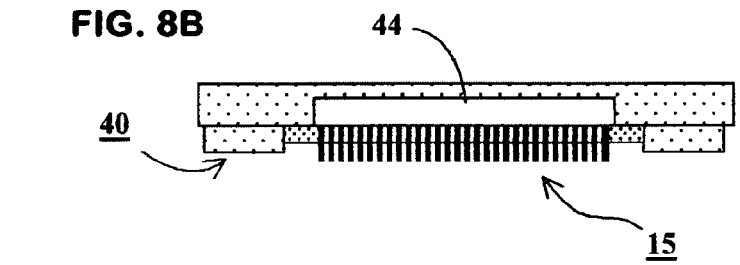
FIG. 8B
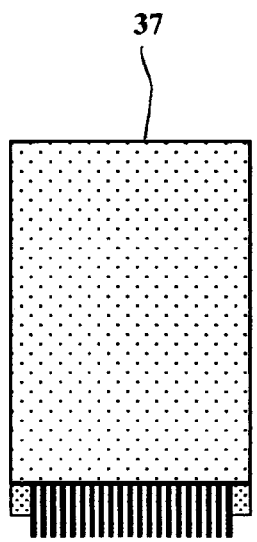
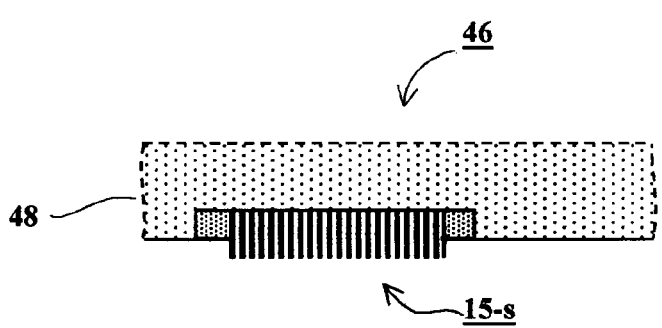
FIG. 8C
FIG. 8D

MICROFABRICATION METHOD BASED ON METAL MATRIX COMPOSITE TECHNOLOGY

CROSS REFERENCE FOR RELATED APPLICATIONS

This application is entitled to the benefit of Provisional Patent Application Ser. No. 60/425,998 filed Nov. 14, 2002.

BACKGROUND

1. Field of the Invention

The present invention is a method of manufacturing microstructural components, microparts assemblies and microparts. More particularly, the invention is a method utilizing Metal Matrix Composites Technology and Low Temperature Superconductors Manufacturing Technology for microfabrication.

2. Description of Prior Art

In manufacturing, forming and removing of substantially homogenous materials are the two major or primary processes. The removing process creates a shape by destroying bonds among particles and removing material. Examples include mechanical turning, drilling and grinding, laser machining, electro discharge machining (EDM), chemical etching, traditional carving etc. The forming process creates a shape from a molten substance, solid particles and binder, electroplating solution, etc. utilizing physical changes which occur due to changing temperature, pressure, chemical composition, etc. usually with the help of a mold or pre-form.

IC-based microfabrication technology (methods used to make integrated circuits) covers both removal and forming processes. All existing microfabrication processes remove substantially homogenous materials according to the 'blueprint', engineering drawings, idea, intuition, etc. The present invention is a material removing process also.

Nevertheless, in contrast with existing technologies, such removal is not according to a 'blueprint'. Removal pattern and creation of a shape are based on composition (non-homogeneity) of the metal matrix composite and properties of the selected etching reagent. Each selected reagent has to remove predominantly one component at each given step of the process. The process resembles creation of a landscape by erosion, in other words a 'blueprint' is in the composite material by itself.

The invention is suitable as a method of fabrication of an array of solid or hollow microprotrusions, micropins, microneedles etc. Generally speaking, arrays of microparts attached to a base or substrate. The microparts could have micron range dimensions and considerable complexity in design, geometry and materials.

An example of such an array is microneedles (microneedles wafer or disk could have many hundreds of very small solid or hollow needles), which can painlessly penetrate into the skin and enable fluid transfer either into the body as a drug-dispensing device, or from the body to sample interstitial body fluids. More precisely, the microneedles wafer, a medical microdevice component, is an example of microparts assembly or microassembly. Another example is an array of micropunches or micropins attached to a substrate. Micropunches are a tool, which could be utilized to fabricate microstructural components. For example, to perforate plastic, paper, and metal foils on micro-scale. Yet another example is an array of microprotrusions utilized as a special surface insert attached to an orthopedic implant to enhance the connection or bond between tissues and an implant.

Metal Matrix Composites (MMC) Technology

Low temperature multifilamentary superconductors are an example of unidirectional (all elements are elongated in one direction) metal matrix composite. Over 90% of all multifilamentary superconductors are made by extrusion and drawing of sizeable (up to 500 kg) billets made of high purity copper with plurality of longitudinal Nb-46.5% Ti alloy elements spaced apart in a predetermined arrangement. The longitudinal Nb—Ti alloy elements, after being reduced to final size and subjected to several aging heat treatments, become superconducting filaments. Depending on the application, wide range of filament diameters (~2–100 microns) and filament number (from few dozens to many thousands) are available in commercial superconductors. The Nb—Ti filaments under 15 microns diameter usually have a sub-micron Nb diffusion barrier. $Nb_3Sn$ type superconductors have a diffusion barrier separating filament array and copper stabilizer. Filaments usually have strength in the 70–140 KSI range. Etching the matrix off will expose practically unbreakable filaments. For example, taking a thin slice of superconductor having 6000 filaments of 12 microns diameter and etching the matrix off 150 microns deep would create 6000 solid microneedles 12 microns in diameter and 150 microns in height. Microneedles made out of commercial superconductor would be located very close to each other due to the fact that superconductor filaments usually occupy 50–60% of the array cross-section. The medical device microneedles are expected to occupy less than 5% of the array cross-section. Superconductor-like structures made with medically acceptable materials and having sufficient distance between filaments/microneedles would make a good microneedle-precursor composite.

See more details on superconductor manufacturing in Ref. 1, Concise Encyclopedia of Magnetic & Superconducting Materials. Editor, Jan Evetts. 1992. Pergamon Press, Inc., Tarrytown, N.Y. 10591-5153, USA. A chapter: "Multifilamentary Superconducting Composites", pages 332–338. And some details in depth Ref. 2, Handbook of Metal-forming Processes, by Betzalel Avitzur, 1983, John Wiley & Sons, Inc., 1020 pages. A chapter: "The Production of Multifilament Rod. The State of the Art—Superconducting Wire", pages 429–432.

Brothers John and Peter Roberts made the first extruded metal matrix composite superconductor. See U.S. Pat. No. 3,625,662 "Superconductor" by Roberts, et al. (Dec. 7, 1971, Brunswick Corp.). This patent teaches the use of extrusion and drawing to fabricate a composite having superconductor filaments embedded in a matrix, which is a non-superconductor. Roberts's wire samples had filaments as small as 0.625 microns. Later those types of structures were named Multifilamentary Superconductors to differentiate them from the tape superconductors. U.S. Pat. No. 5,127,149 "Method of production for multifilament niobium-tin superconductors" by Ozeryansky, (Jul. 7, 1992, Intermagnetics General Corp.) teaches the use of extrusion and drawing to fabricate an assembly incorporating complex shapes and combination of materials with extremely poor matching of properties.

Another metal matrix composite example is stainless steel filaments in mild steel matrix. In U.S. Pat. No. 3,379,000 (Apr. 23, 1968) "Metal Filaments Suitable for Textiles" by Weber et al. MMC technology is utilized for manufacturing high quality stainless steel fibers. Billets were constricted by extrusion and brought to final size by cold drawing. Low carbon steel matrix was etched off in-line exposing the bundle of fibers. In the 1970's Brunswick Corporation manufactured high quality metal fibers utilizing MMC technology. Roberts brothers also applied MMC technology to fabricate micro-structural components. For example, U.S. Pat. No. 3,506,885 "Electric Device Having Passage Structure Electrode", by Roberts, et al. (Apr. 14, 1970) and U.S. Pat. No. 3,868,792 also by Roberts, et al. (Mar. 4, 1975). Extrusion and drawing was utilized to fabricate "collimated hole structure" or a "passage structure" (structure having plurality of micro-orifices) suggested for electrolytic capacitors and as a tip (structure having multiplicity of small nozzles) for a drilling device.

Potential uses of MMC technology to fabricate unique microstructural components were first recognized in the early 1950's. See U.S. Pat. No. 2,499,977 (Mar. 7, 1950) "Method of Forming Gridlike Structure" for high frequency electric discharge devices by W. J. Scott. The method comprises assembling into a bundle a plurality of rods, which have been coated with a metal, of which the grid has to be formed. Surrounding the bundle with a tube and reducing the cross sectional area of the bundle-in-the-tube by drawing. After the bundle has been reduced to final size and cut in sections the core rods are removed by a suitable chemical reagent, which does not attack the grid material. U.S. Pat. No. 2.628,417(Feb. 17, 1953) "Method of Preparing Perforate Bodies" disclosing a method of fabricating of very small orifices by Ivan Peyches. A particular example is making a spinneret (a disk with a plurality of very small orifices) for manufacturing of synthetic fibers. Peyches suggests using a drilled billet with holes filled with glass, extruding said billet to the designated diameter, slicing the material to form thin sections and leaching out the glass cores from those sections.

Microneedles Medical Devices

Skin is a protective multi-layer barrier between the body and environment. At approximately 200 microns thick, the epidermis is the outermost layer of skin and it contains many of the components that give skin it unique barrier-protective characteristics. The outermost layer of epidermis, the stratum corneum, which is about 15 microns thick when dry and about 50 microns when fully hydrated, acts as a barrier for an extremely large variety of compounds. The stratum corneum is a heterogeneous layer of flattened, relatively dry, keratinised cells with a dense underlying layer commonly called the "horny layer" is both tough and flexible, with a significant degree of elasticity. These characteristics make the stratum corneum unique and an effective barrier, resistant to penetration. Beneath the epidermis is the dermis, which houses blood vessels and nerve endings. Millions of small capillaries feed the upper levels of the dermis. These capillaries extend to just above of the nerve endings that also are located in the dermis.

Drugs are commonly administered orally, however, many drugs cannot be effectively delivered in this manner, due to their degradation in gastrointestinal tract and possible elimination by the liver. Furthermore, some drugs cannot effectively diffuse across the intestinal mucosa. The use of needles is another well-developed and widespread technique for delivering drugs across biological barriers. While effective for this purpose, needles are cumbersome; generally cause pain, damage to skin at the site of insertion, bleeding, risk of infection and disease transmission. Similarly, current methods of sampling biological fluids are invasive and bear the same disadvantages. Needle technique also is not convenient for the long-term, controlled continuous drug delivery. Current topical drug delivery methods are based upon use of penetration enhancing methods, which often cause skin irritation, and the use of occlusive patches that hydrate the stratum corneum to reduce its barrier properties. Only small fractions of topically applied drugs penetrate skin, usually with very poor efficiency.

Responding to the long felt need existed in medical art Martin Gerstel, et al. had disclosed the feasible alternative to drug delivery by injection in U.S. Pat. No. 3,964,482 (1976). The disclosed device designated for "administering a drug comprising a plurality of projections, a drug reservoir containing a drug, and were the projections extend from the reservoir and are adapted for penetrating the stratum corneum for percutaneously administering a drug from the reservoir to produce a local or systematic physiological or pharmacological effect." An array of either solid or hollow microneedles is used to penetrate through the stratum corneum, into the epidermal layer, but not to the dermal layer. Fluid is to be dispensed either through hollow microneedles, through permeable solid projections, or around non-permeable solid projections that are surrounded by a permeable material or an orifice. The microneedle size is disclosed as having a diameter of ~125 to 1700 microns, and a length in the range of 5–100 microns.

According to Gerstel the term "percutaneous" means penetration through the skin "to the local or systemic circulatory system by puncturing, scraping, or cutting the stratum corneum" but not penetrating "to substantial extent the interior layers of skin." Once a drug penetrates through the stratum corneum, with the aid of a microneedle drug delivery device, penetration through the remaining layers of the skin proceeds readily. Having microneedle heights chosen to avoid the nerve endings, which are up to 100 microns deep, drug injections will be painless.

The ~125 microns diameter needles were the smallest needles available in the 1970's. If Gerstel had available good, strong and reasonably priced arrays of hollow microneedles, one could imagine, his drug delivery device would improve quality of life for millions people. Even today, more than twenty years later, microneedles devices still are not available to the public.

Another structure, disclosed in U.S. Pat. No. 6,083,196 by Trautman et al. (Jul. 4, 2000) and U.S. Pat. No. 6,219,574 by Cormier et al. (Apr. 17, 2001, both ALZA Corp.) for a device, which enhances transdermal agent delivery and sampling. It employs a plurality of solid metallic microblades, etched and mechanically bent from thin (~100 micron thick) titanium sheet. U.S. Pat. No. 6,050,988 by Zuck (Apr. 18, 2000), also ALZA Corp., disclosed a structure made of thin metal sheet with microblades that do not require bending. Zuck utilizes assemblies of rather high complexity in his device.

Microfabrication

Much research has been directed towards the development of microneedles utilizing micro-fabrication techniques. These microfabrication processes are based on well-developed methods used to make integrated circuits (IC-technology) and other microelectronic devices. The approach promises the possibility of producing numerous, small needles, which are sufficient to penetrate stratum corneum. There are a number of patents granted and pending; utilizing one or more microfabrication processes. Those processes, for example, are described in depth in: Ref.3, Fundamentals of Microfabrication by Madou, Mark J. CRC Press, LLC 1997, 589 pgs. See Table of Content and pages 328–335.

For example, U.S. Pat. No. 6,334,856 to Allen et al. (Jan. 1, 2002, Georgia Tech) discloses several microfabrication methods of making microneedles. A preferred method of fabricating hollow metal microneedles utilizes the micromold electroplating techniques. First electroplating the micromold forms an array of hollow microneedles, then the micromold is removed from the microneedle array. The Georgia Tech patent also discloses fabrication of arrays of microneedles utilizing several micromachining methods, and plastic microneedles by injection micromolding technique. Another example, U.S. Pat. No. 6,331,266 (by Powel, et al. Dec. 18, 2001) and U.S. Pat. No. 6,471,903 (by Sherman, et al. Oct. 29, 2002), in which plastic microneedles are micro-molded by injection molding, and compression molding or embossing. In U.S. Pat. No. 6,533,949 (by Yeshurun, et al. Mar. 18, 2003) hollow microneedles are processed by improved micromachining methods.

Microfabrication is well developed and highly diversified technology. The microfabrication methods for the manufacture of microneedles have exhibited a lot of progress in recent years. Nevertheless, those methods are generally time consuming, expensive and the mechanical properties of the microfabricated microneedles are far less than what is considered mandatory for stainless steel hypodermic needles.

IC technology can't utilize cold work texture essential to achieve combination of strength, hardness and ductility required for hypodermic needles. Hypothetical example, microneedles are micromachined from a high strength yet still substantially ductile titanium alloy substrate. Cold work, more precisely cold rolling, is the most efficient way to fabricate 300–400 microns thick titanium sheet. The high strength is mainly the result of cold work texture, in this example it is a cold rolling texture, specifically texture developed in direction of rolling or longitudinal direction. Titanium microneedles micromachined from such substrate will have high strength texture in transverse (wrong) direction. Transverse texture will make microneedles predisposed to fracturing. The matter of fact, any elongated element having transverse texture is highly predisposed to fracturing.

One shortcoming of microneedles made by micromachining techniques is the brittleness of the resulting microneedles. Microneedles made from silicon or silicon oxide are highly brittle. As a result, a significant proportion of the microneedles may fracture from stress during penetration, leaving needle fragments within the tissue. Microneedles made by electroplating are not as brittle as those made of silicone or silicon oxide, nevertheless, electroplated structures do not have the combination of strength and ductility desirable for hypodermic needles. Plastic needles do not have the strength and hardness to hold "the edge", which is critical for performance of hollow needles having thin wall sections.

Microfabrication requires sophisticated and expensive equipment and a highly trained workforce. Packaging or assembling of microparts is always a difficult and costly operation, which also requires complex equipment. Packaging expenses frequently exceed the cost of fabricating a micro part. Accordingly, a continuing need exists in the industry for an improved method for the manufacture of microneedles.

SUMMARY OF THE INVENTION

The invention is a method of manufacturing microstructural components, microparts and microparts assemblies utilizing Metal Matrix Composite and Low Temperature Superconductor Manufacturing Technologies. The method of invention is suitable for fabricating microneedles—a medical device component having micron features. According to the teaching of the invention a method is provided for manufacturing a wafer or disk having an array of microprotrusions, solid or hollow, protruding from a substrate.

The method comprising the steps of:
1. Fabrication of a unidirectional elongated metal matrix composite made of materials selected to allow removal of matrix without damaging filaments. The filaments, or the longitudinal elements, being the protruding parts after partially etching the composite matrix off. The metal matrix composite structure will define the structure of the micro-assembly. Considering hollow protruding parts: cores of those parts have to be made of materials, which could be etched out without damage to a matrix or protruding parts.
2. Cutting metal matrix composite to form slices of desirable thickness.
3. Developing an arrays of microparts, microprotrusions, and microneedles by etching.

Accordingly, Several Objects and Advantages of the Present Invention are:
(1a) to provide a method for efficiently manufacturing microstructural components, microparts and microparts assemblies, and also small parts and small parts assemblies;
(2a) to provide a method of manufacturing a micro-device components in a cost efficient manner;
(3a) to provide reliable and simple method of manufacturing a micro-device components with plurality of hollow or solid microprotrusions (microneedles, micropins, etc.) having no length limitations;
(4a) to provide a method of manufacturing a micro-device component having high strength and virtually unbreakable microneedles;
(1b) to provide a method of manufacturing very strong microneedles, which could be bent severely without breaking;
(2b) to provide a method of manufacturing micro-device components, which have sufficient strength for convenience and ease of handling and assembling,
(3b) composite slices may be mounted or molded into a housing or base. Said housing protects the microneedles throughout the fabrication process and also facilitates handling, assembling, storage and transportation of the microparts;
(4b) to provide a method of manufacturing a micro-device having a plurality of hollow or solid microneedles with a microneedles density of but not limited to about one to about 100 per square millimeter;
(1c) to provide a method of manufacturing microneedles, which offer a natural separation in the context of this method between microneedle manufacturing and medical device fabrication;
(2c) to provide a method of manufacturing a micro-device having a plurality of hollow or solid microprotrusions with no limitation for protrusions shape and distance between those protrusions;
(3c) to provide a method of manufacturing a micro-device having a plurality of hollow or solid microprotrusions, which are metallurgically bonded to the substrate;
(4c) to provide a method of manufacturing microneedles mechanically strong enough for penetrating and abrading the stratum corneum for repeated use as a skin perforator;

(1d) to provide a method of manufacturing microneedles mechanically sufficiently strong for penetrating stratum corneum for the one-time repeated use to administer medication injections designated to saturate with a drug large areas of skin;

(2d) to provide a method of manufacturing micropins or micropunches mechanically strong enough for penetrating plastic, paper, and metal foils;

(3d) to provide a method for manufacturing arrays of high strength micropins and micropunches to be utilized as a microfabrication tool;

(4d) to provide a method for manufacturing arrays of high strength microprotrusions to be utilized as a special surface modulus or insert for orthopedic implants.

(1e) to provide a method of manufacturing a micro-device component—microneedles (more precisely—microneedle wafers mounted into a base or housing) as a readily available and inexpensive medical device component;

(2e) to provide a simple method of manufacturing microneedles arrays with every microneedle having an axial gap or a missing sector of variable width.

(3e) to provide a method of manufacturing microparts, microprotrusions and microneedles, and arrays of microparts, microprotrusions and microneedles, which allows simple and inexpensive noble metal cladding of each element (inside and/or outside);

(4e) to provide a method of manufacturing arrays of microparts, microprotrusions and microneedles, with a substrate having controlled porosity;

(1f) to provide a method of manufacturing microparts, microprotrusions and microneedles, and arrays of microparts, microprotrusions and microneedles, which allows more then one material in making of each component;

(2f) to provide a simple method of changing geometry of microparts, microprotrusions, and microneedles tips or upper extremities;

(3f) to provide a simple method of changing diameter of upper section of microparts, microprotrusions and microneedles after parts were formed by final etching.

These objects, as well as other objects, features and advantages will become more readily apparent from the following detailed description, drawings, and accompanying claims.

DRAWING FIGURES

FIGS. 1, 1A and B Schematic of the process of fabricating a microparts assembly.

FIG. 2 The Microfabrication Process Diagram with a schematic of scaling and fabrication.

FIG. 3 Schematic of cross-section of the gun-drilled billet with subelements.

Figure 4:
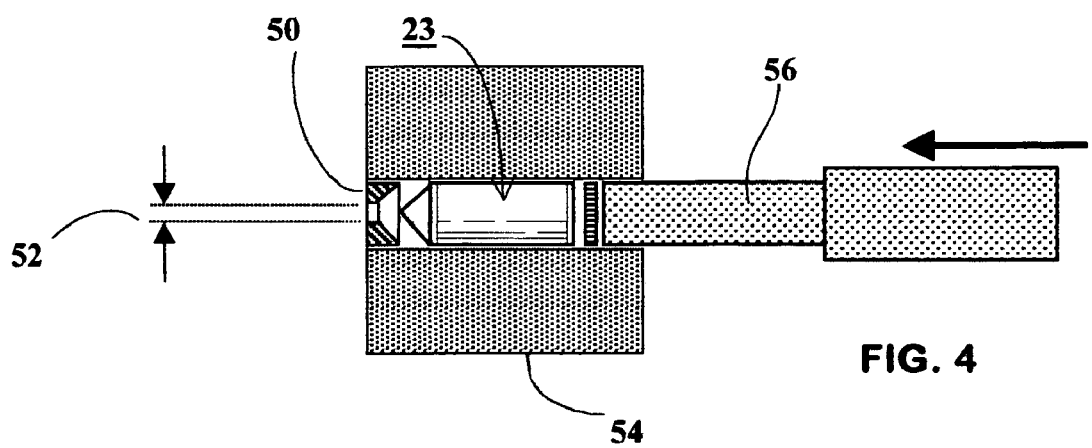

FIG. 4 Schematic of high temperature extrusion.

Figure 5A:
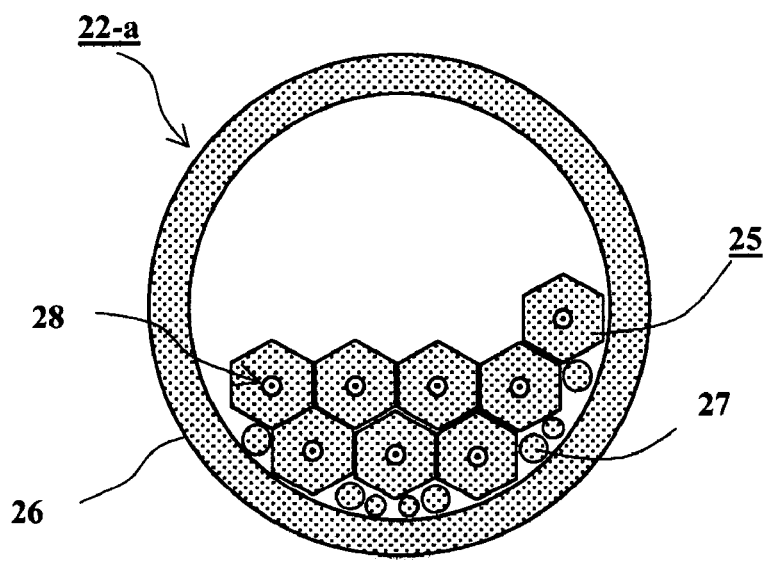

FIGS. 5A and B Schematic of billet assembling or gun-drilling to fabricate a hex-pattern.

Figure 6A:
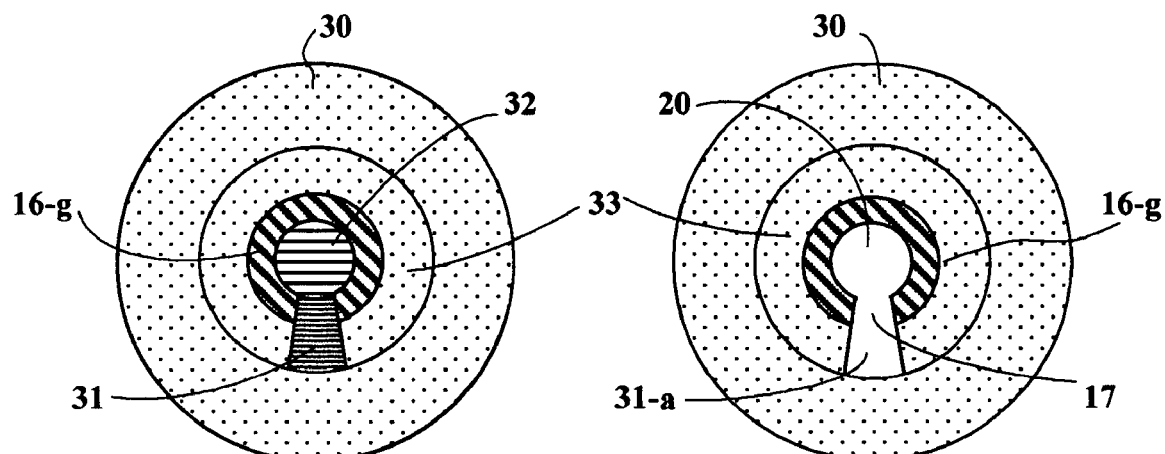

FIGS. 6A, B, C Schematic of various subelement sections with microneedles of different shape at final size before and after etching.

Figure 7A:
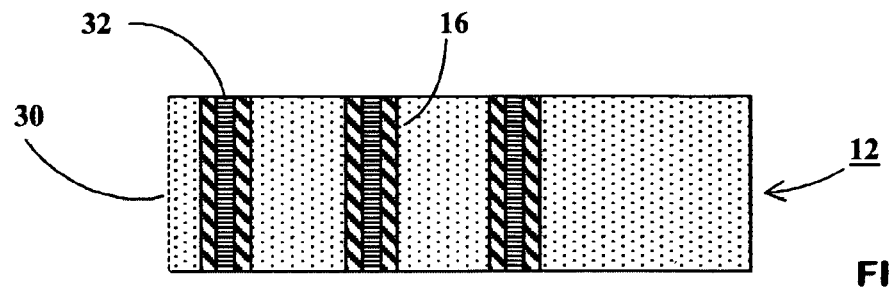

FIGS. 7A, B, C, D and E Schematic side cross sectional view of etching of a slice of the metal matrix composite and forming various microprotrusions.

FIGS. 8A, B, C and D Examples of microneedles and microprotrusions devices.

Figure 9A:
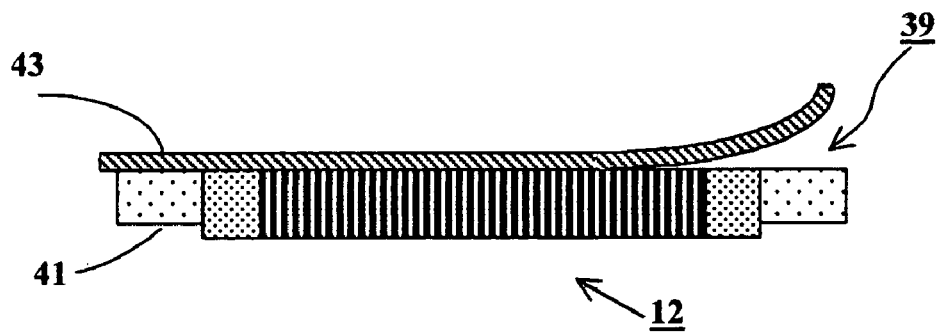

FIGS. 9A and B Schematic of etching the microneedle slice mounted in the housing.

Figure 10A:
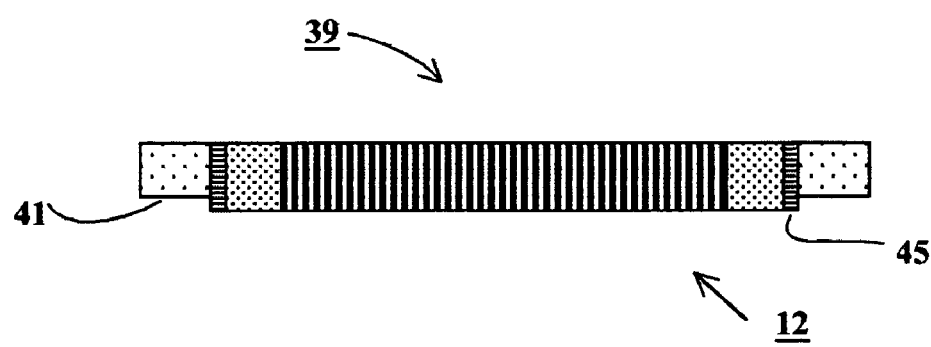

FIGS. 10A and B Schematic of etching the microneedle slice having non-etching barrier.

REFERENCE NUMERALS IN DRAWINGS 11 metal matrix composite rod at final size;
12 slice cut of metal matrix composite rod;
14 microneedles or microprotrusions array;
15 microneedles disk or wafer, (microneedles array attached to a substrate forms microneedles disk 15);
15-*p* micropunch array disk;
15-*s* microprotrusions surface array insert or microsurface modulus (an orthopedic implant insert);
16 hollow microneedle or hollow microprotrusion, if matrix completely etched off—hollow tubular micropart; surrounded by a matrix material 16 is a longitudinal element or a filament 16-*e*;
16-*c* microprotrusion having a core etched out at the tip forming a cup-shaped configuration;
16-*e* longitudinal element or a filament surrounded by a matrix material;
16-*g* microneedle having a small axial gap;
16-*h* microneedle having an axial gap and a core etched out at the tip, forming a pocket;
16-*p* partially formed needle, a matrix etched just enough to expose the tip of microprotrusion;
16-*r* rectangular shape tube—'microneedle in making';
16-*s* solid microprotrusion or micropin;
16-*t* tube at subelement size—'microneedle in making';
16-*u* u-shape tube—'microneedle in making';
16-*w* microneedle with a wide axial gap;
17 axial gap;
18 base or substrate—remnants of a matrix partially etched off to form microneedles;
19 gun-drilled hole in the hex-pattern billet;
20 hollow microneedle ID;
21 micro-orifice;
22 gun-drilled billet cross section with subelements inside, the example of circular pattern;
22-*h* schematic of billet with gun-drilled hex pattern;
23 billet positioned inside of extrusion press liner;
24 round subelement rod with subelement-rod-core 28;
(the word subelement-rod-core has hyphens to avoid confusion between subelement core and longitudinal element or microneedle core);
25 hex-shaped subelement;
25-*f* imaginary hex marked by dotted line;
26 billet can—a large tube utilized for billet assembly;
27 billet assembly spacer;
28 subelement-rod-core with a tube ('microneedle in making');
the tube also has a core, that core being removed will form a hollow shaft;
28-*r* subelement-rod-core with rectangular hollow tube ('microneedle in making');
28-*u* subelement-rod-core with half circle or u-shape tube ('microneedle in making');
29 half round spacer;
30 matrix (matrix of metal matrix composite);
30-*p* partially etched matrix;
31 trapezoidal shape spacer;
31-*r* core of rectangular tube at subelement size (rectangular microneedle in making);
31-*a* micro-orifice connected with ID—appears after spacer 31 is etched out;
31-*u* etched-out segment;
31-*p* spacer,
31-*b* wide etched-out spacer;
32 etched-out core;
32-*u* etched-out core of a u-shape tube;

32-s etched-out center of subelement-core,
33 core encasing tube;
34 platinum layer;
35 microneedle syringe attachment hub;
36 main body of syringe microneedles attachment;
37 micropunch extension rod;
38 syringe;
39 housing with metal matrix composite slice in—the microneedle housing assembly before etching,
40 microneedle housing assembly;
41 microneedles housing rim or microneedles housing;
42 simple microneedle patch;
43 peel-off backing for etching assistance;
44 drug reservoir;
45 non-etching barrier;
46 orthopedic implant assembly with microprotrusion surface array insert 15-s fitted in;
48 section of an orthopedic implant (an artificial bone);
50 extrusion die;
52 diameter of the extrudate;
54 extrusion press liner,
56 extrusion press ram.

DETAILED DESCRIPTION OF THE INVENTION

The invention is the method for manufacturing of microstructural components, microparts assemblies and individual microparts. More precisely method is for manufacturing a wafer or disk having an array of micro protrusions, protruding from and bonded to a substrate. Each protrusion constitutes an individual micropart, which could be solid or hollow, having simple or complex geometry, made of one or several materials.

The method comprising the steps of:
1. Fabricating of unidirectional metal matrix composite having a structure, which define the microstructural assembly and microparts.
2. Preparation of the composite slices or sections.
3. Developing microparts assembly by partial etching of matrix, or developing individual microparts by etching a matrix entirely off. Developing the hollow microneedles by etching out the microneedles cores.

A microneedles wafer and an array of micropunches have a simple geometry and are convenient examples of microparts assemblies because fabrication challenges are substantially in dimensions.

A microneedles wafer is an assembly made with plurality of very small solid or hollow needles attached to and protruding from a substrate. Viewed in a microscope microneedles array look like a small brush with short bristles. For example, a one-centimeter square microneedle wafer could have many hundreds microneedles up to 250 microns in height and few microns in diameter (practical diameter range up to 70 microns).

Micropunches, more precisely, the array of micropunches attached to a substrate is a tool, which could be utilized for fabrication of microstructural components. Visually it would be very difficult to distinguish micropunches from solid microneedles if they have the same pattern and size of pins. Apparently micropunches do not have to be made from medically acceptable materials.

The illustrated embodiments FIG. 1 provides schematic example of fabrication of microparts assembly. More precisely FIG. 1 shows that a microneedle disk or wafer 15 is made utilizing a metal matrix composite rod 11 (having plurality of longitudinal elements 16-e) by slicing that rod to produce a slice 12 and, finally, etching slice 12 to form a microneedle array 14. The enlargement shows cross-section of wafer 15 with microneedles 16 protruding out of a substrate 18. Etching also forms the microneedle hollow shaft or (ID) inside diameter 20.

Altogether microneedles array 14 attached to a substrate 18 is microneedles wafer or disk 15.

The FIG. 1A is side cross sectional view, which shows the edge of the wafer with microneedle 16 protruding out of substrate 18 like 'a press-fit hollow pin'. The FIG. 1A also shows an orifice 21, more precisely a micro-orifice, through substrate 18.

Any core or a filament (an additional longitudinal element) in the matrix after having been etched out will leave a micro-orifice in its place. Small copper rods introduced at time of billet assembling would be sufficient to be such additional longitudinal elements for this purpose. The substrate having plurality of micro-orifices would be an example of a porous substrate. By controlling shape spacing, size and quantity of the additional longitudinal elements this technology allows fabricating substrate with precisely controlled porosity.

The FIG. 1B is side cross sectional view, which shows microneedle 16-w having a wide axial gap 17. The gap 17, example of a feature having longitudinal geometry, could vary in width from near zero to 180 degrees of circle and even more. Clearly it could be more than one gap. Also, it is obvious that gap spacer 31-w, see FIG. 6B, (also is example of a feature having longitudinal geometry) does not have to be made of copper only and does not have to be removed completely.

Fabricating a Metal Matrix Composite

An elongated and unidirectional (aligned in single direction) metal matrix composite is, generally speaking, microparts assembly or microstructural component precursor, more precisely, in these examples it is the microneedles wafer or micropunches disk precursor. Therefore, design, structure and materials the metal matrix composite is made with will define design and structure of the microstructural component.

Composite structure comprises essentially of a matrix and longitudinal elements, for example features 16e (FIG. 1) usually referred as filaments. In MMC field filaments always have small diameter at final size. Nevertheless, for microfabrication purpose filaments could be of relatively large size also. In strength of that a term longitudinal elements is more accurate and having a lot of sense. The filaments will become microparts if matrix is etched out completely. Micropart length is equal to composite slice thickness. Filaments could have special shape and/or tubular geometry with a metal core.

Each microneedle 16 (FIG. 1, 1A, 1B) is metallurgically bonded to substrate 18, plus all elements of microneedle wafer are metallurgically bonded to each other. Microneedles are strong, precise and virtually unbreakable. For example, superconductor filaments, made of Nb or Nb—Ti alloy, (after matrix been etched off) could be bent-unbent 180 degrees repeatedly without breaking. Due to cold work at final processing by drawing, microneedles strength UTS could exceed 140 KSI. The substrate (or matrix) can be made of high strength metals such as stainless steel or titanium alloys, which are conducive to positive mechanical assembly with an injection device. If matrix and filaments are selected to target greater strength, the UTS of micropins (preferably solid simple shapes) could exceed 200 KSI.

The Microfabrication Process Diagram with a schematic of dimensional scaling and fabrication, FIG. 2, outlines step-by-step fabrication of microparts assembly including main steps of manufacturing a metal matrix composite. The metal matrix composite billets are assembled with building blocks called subelements. Subelements have to be fabricated as a separate and independent task. Parameters of subelement will define parameters of microparts and microneedles. Subelement billet is extruded (at that stage it is called the extrudate) and drawn to final (composite billet assembly) size; at this stage it is called a subelement rod or subelement. For example, subelement rod 24 is the building block of a composite billet 22 (FIG. 3).

Subelement concept is extensively used in superconductor manufacturing.

The Metal Matrix Composite and Superconductor Technologies have developed procedures and techniques for scaling-down large elements to very small dimensions. In example the below a 25 mm diameter subelement core will be reduced down to 25 microns and will become a microneedle. That is a 1000 times reduction in diameter. Even more noteworthy, this reduction in diameter translates into a one million times reduction in the cross sectional area. If we would decrease the diameter of microneedles in this example to 12 microns the cross sectional area reduction would be four millions times. Those numbers indicate that this method has to be highly cost effective.

Fabrication of the microneedles precursor metal matrix composite is substantially similar to fabrication of the Low Temperature Superconductors. The major process milestone is fabrication of a composite billet for extrusion. The billet design will define the geometry and structure of the metal matrix composite and eventual geometry and structure of the microneedles wafer.

The Process Diagram (FIG. 2) shows that composite billets are assembled, extruded (at this stage it called second extrudate) and drawn to final size (or wafer diameter). Next steps are slicing composite rod and etching slices to form microneedles. Based on fabrication method there are three types of composite billets: drilled or more precisely gun-drilled billets, assembled billets, and a combination thereof.

Gun-drilled billets a round metal bar up to 12 inches in diameter and up to 40 inches long is gun-drilled with a number of holes all the way through from face to face. The holes usually arranged in two major patterns: circular pattern and hex pattern. Subelement billets usually have a small number holes starting with one. The FIG. 3 shows schematic cross-section of a gun-drilled billet 22 having circular pattern with subelement rods 24 inserted in each hole. The (FIG. 5B) shows hex-pattern drilled billet 22-h.

Assembled billets: See FIG. 5A, hex shape subelements 25 are assembled inside of a can up to 12 inch diameter and up to 40 inches long. Spacers 27 are utilized to fill all voids. A billet made by assembling hex-shape subelements, FIG. 5A, is less expensive than gun drilled one. But occurrence of inferior bond between elements could cause thin wafer to fracture. It is important to note that subelement billets made by assembling, not gun drilling, are less susceptible to cracking problems because double extrusion (see fabrication diagram FIG. 2) develops superior metallurgical bond between elements.

A subelement billet, if large number of microneedles is a target, could have plurality of elements or subelement-cores 28. A subelement-core could also be made by extrusion of a billet containing a plurality of elements. For example, the first stage (first extrusion) subelement core has 100 longitudinal elements. The second stage subelement core (double extrusion) also has 100 longitudinal elements made with the first stage material. Multiply 100 by 100—subelement in this example will have 10,000 longitudinal elements. If we will use this double extrusion subelement to fill gun-drilled billet 22 having 61 holes, number of filaments in the final (triple extrusion) metal matrix composite will be: 610,000 (10,000 by 61).

Combination billets have more than one subelement rod inserted in the gun-drilled holes. For example, assuming we assembled the 61 hole billet with 7 double extrusion elements (instead of one double extrusion element in example above). Final (triple extrusion) metal matrix composite will have 4270 000 filaments (61 by 7 by 10,000 equal 4,270,000).

Non-Etching Barrier.

Figure 9B:
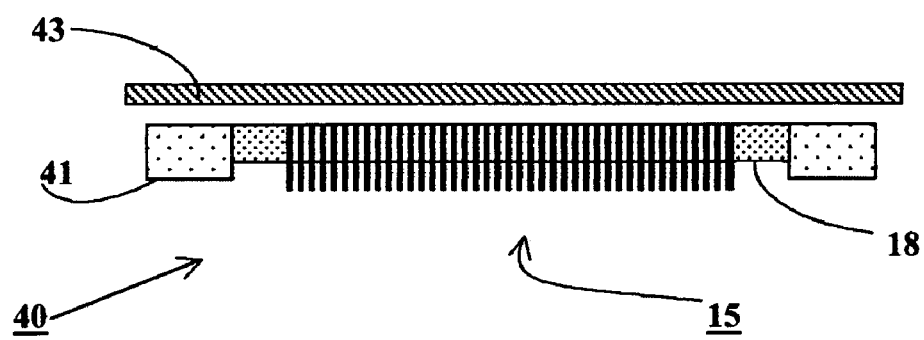
Figure 10B:
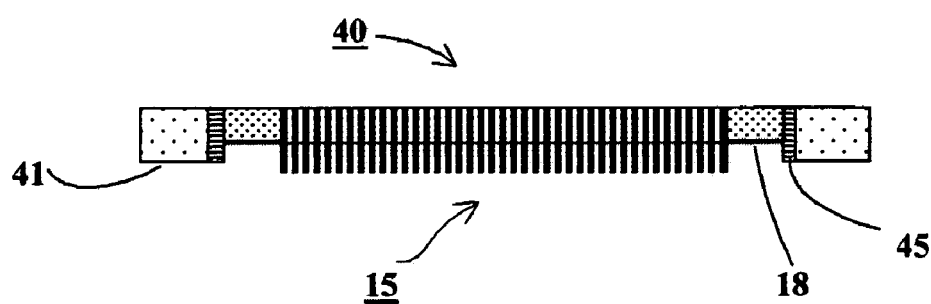

The microneedle wafer 15 is press fit, snap-in fit or molded into a microneedle housing 41, FIGS. 9B and 10B. At time of etching acid might find its way between a housing and a microneedle wafer. An acid resistant or non-etching barrier 45, FIGS. 10A and B may be useful to prevent loosening of a composite slice 12 fit and eventually microneedle wafer 15 fit in the microneedle housing 41. The non-etching barrier could be made by extrusion of a composite billet having metal sheet (future non-etching barrier) around the gun-drilled billet 22 (FIG. 3), or 22-h (FIG. 5B), or assembled billet 22-a (FIG. 5A).

Superconductor manufacturers frequently utilize all kinds of barriers in their designs.

Following standard billet manufacturing practice, a billet containing the non-etching barrier has to be sealed inside of a can or jacket. Furthermore, any billet made of materials, which could be damaged by being exposed to air at elevated temperature (temperature of extrusion) has to be sealed inside of a can.

Further on we will use the words subelement-rod-core or subelement-core to distinguish a microneedle core from a subelement core.

Whatever the avenue is taken to construct a composite billet, a gun drilled hole for the subelement-rod-core 28 (FIG. 3) to fit-in will always be too small for drilling. (For example, 254 mm (10 inch) diameter billet is going to be reduced to final size of 12.7 mm (0.5 inch) and final needle size at that diameter is chosen to be ~25 μm (~0.001 inch). To calculate how many times the future needle will have to be reduced (to reach 25 μm target diameter) the starting composite billet diameter 254 mm (10 inch) has to be divided by final wafer diameter (0.5 inch), which is twenty (20). That means the subelement-core 28 (future microneedle) at size of assembling composite billet has to be twenty (20) times larger than the final microneedle (25 μm by 20=500 μm). In other words—subelement rod 24 has to have core diameter 500 μm (0.020 inch). It is impractical to drill 0.5 mm diameter hole longer than one centimeter.

Depending on billet length and materials, for production-size billet a reasonable minimum gun-drilled hole diameter starts with ~5.8 mm (~0.230 inch). Subelements have to be fabricated to overcome those drilling limitations. For the above example, a subelement rod 24 (diameter 5 mm), with subelement-core 28 diameter of 500 microns (0.020 inch) has to fit inside of composite billet gun drilled holes with diameter 5.8 mm (~0.230 inch).

Figure 5B:
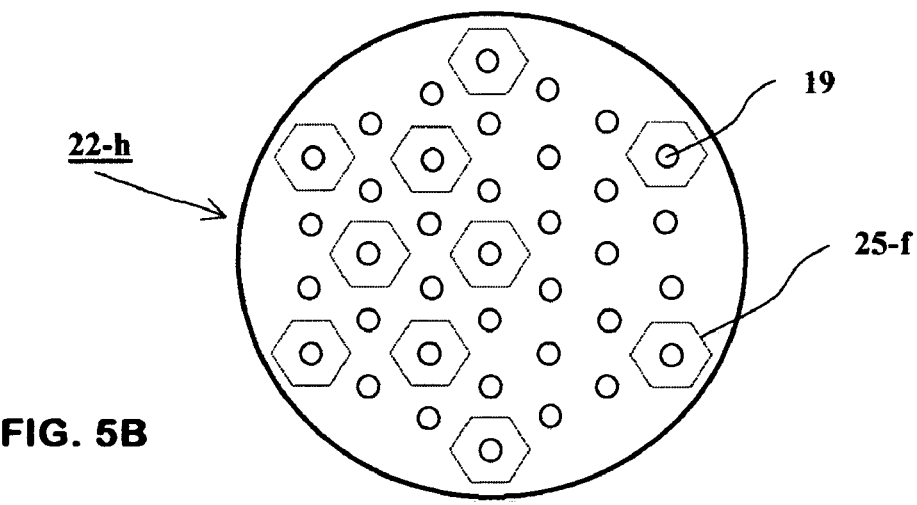

In the case of assembled billets FIG. 5A hex shape subelements 25 are assembled inside of a can and, as is evident from FIG. 5B, the cross section (and dimensions) of hex shape subelement has to be even larger, than of the round one, to provide necessary amount of matrix. Subelement-core 28 (FIG. 3 and FIG. 5A) will be reduced uniformly to final size together with all other elements of a composite billet.

The FIG. 3 shows subelement-cores at a composite billet assembly size; in light of that the elements 16-*t*, 16-*r* and 16-*u* are not microneedles yet but very small tubes. Subelement-core 28-*r* is a schematic of making rectangular shape microneedle and subelement-core 28-*u* is a schematic of making of u-shape microneedle (FIG. 3). (In the above example the element 16-*t* has a diameter 500 microns (0.020 inch.)

It is important to note that the subelement-core diameter at subelement billet assembly size will be fifty (50) times larger. Assuming subelement billet diameter 254 mm or 10 inch (10 divided by 0.200=50). In this example subelement rod 24, FIG. 3, is product of 254 mm (10 inch) extrusion and drawing to final size 5 mm (~0.200 inch).

Refer to FIG. 2—beginning of the process, in the above example subelement-core at subelement billet assembly (254 mm) size will be ~25 mm or ~1 inch (0.020 multiplied by 50). Obviously it is relatively easy, working with a core that large, to introduce all kinds of features. The standard metal fabrication methods are perfectly suite for it. This is why it is so simple to fabricate microneedles of various configurations including configurations of considerable complexity. For example, double and triple wall tubes, configurations with fins, membranes and dividers, thin and thick sections, protrusions and gaps. Also complex shapes combining features of longitudinal and concentric geometry (for example double wall tube with a gap). Furthermore microneedle design could combine different materials in its geometry. The previously discussed axial gap is an example of a feature of longitudinal geometry and noble metal barriers are features of concentric geometry.

In some simple cases repeated co-drawing technique could be enough to make a single-core subelement. A subelement with more than one core preferably should be made only by extrusion. One subelement billet could supply enough material for number of composite billets. For example, if subelements occupy 20% of cross-section of the composite, one subelement billet will be needed for five composite billets.

The FIG. 6A, B, C show schematic of subelement cores of various geometry at the final microneedle wafer size (12.7 mm diameter in our example). In light of that elements 16-*g* and 16-*w* are microneedles at the final size.

It has to be noted that all elements of the composite (or subelement) at any size and any stage of the processing have the same ratio between components.

The FIG. 6A shows microneedle 16-*g* having a gap 17. More precisely it is the narrow axial gap (see FIG. 1B), extending from the tip of the needle all the way through to the bottom of base 18. The gap, or missing segment of the needle 16-*w* can be seen in a side cross sectional view of FIG. 1B and a transverse cross sectional view FIG. 6B. The needle 16-*w* has a wider axial gap than needle 16-*g*.

The left side of FIGS. 6A, B and C show the microneedles 16-*g* and 16-*w* before etching out core 32 and the right side of FIGS. 6A, B and C show the hollow microneedles 16-*g* and 16-*w* after etching.

Etching a matrix does not change the microneedle dimensions or ratio between elements of the composite.

Figure 7B:
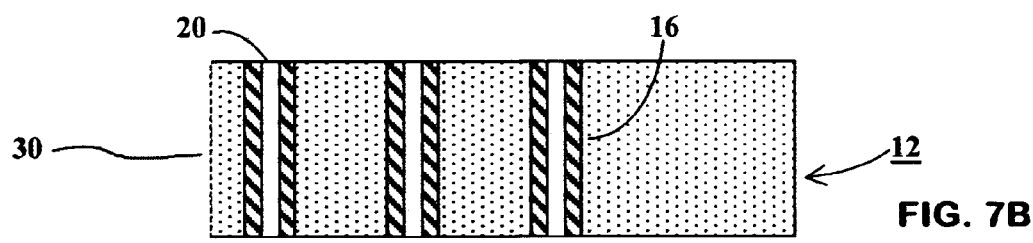

The etching process in details could be followed step-by-step in a side cross sectional view of a slice, (see FIGS. 7A, B, C, D and E) being etched. In the FIG. 7A the microneedles 16 are completely surrounded by matrix material before etching. The microneedles 16 are absolutely identical before and after the core is etched out (FIG. 7B) forming hollow shafts. Finally, the upper half of the matrix is etched off (FIG. 7D) forming a microprotrusion. The FIG. 7E is a schematic illustration—cross-sectional view showing a variety of microprotrusions: a solid micropin 16-*s*, a solid microprotrusion with a cup-shaped tip 16-*c* and a solid microprotrusion with a gap and pocket-shaped tip 16-*h*. Configuration 16-*h* would appear if microneedle 16-*w* (see FIG. 1B) would have a core made with a matrix material or material similar to the matrix. Respectively, the configuration 16-*c* would appear if microneedle 16 (see FIG. 1A) would have a core made with a matrix material or material similar to the matrix.

In the FIG. 6A (left side—before etching) subelement core is located inside of a core-encasing tube 33 and the etched-out core spacer 31 occupies sector of microneedle 16-*g* and the tube 33. In the FIG. 6A (right side—after etching) microneedle core 32 and core spacer 31 are etched out revealing axial gap 17 in microneedle 16-*g* and an orifice 31-*a*, which is connected and communicating with microneedle inside diameter 20.

The orifice 31-*a* actually is expanding the cross-section of opening available for the fluid to go through. Also that type of orifice could provide acid access to core from a side thus speeding etching of the core 32. Orifice 31-*a* actually is a feature of a substrate with controlled porosity.

Core-encasing tube 33 (FIG. 3) is also utilized in subelement-core 28-*r* together with a half-round spacer 29 to fabricate rectangular microneedle, and subelement-core 28-*u* to fabricate the u-shape microneedle. Generally speaking, tube 33 may be needed to hold together elements the subelement-core being fabricated when microneedle shape differs from a simple round configuration. All kinds of solid or hollow shapes could be machined, crafted and assembled, like a "puzzle", inside of the core-encasing tube.

A gap in the needle, more precisely the gap in the section of needle adjacent to a tip, is expected to prevent tissue occlusion from blocking fluid flow.

Metal matrix composite fabrication technology allows simple and economical metal cladding. Introducing metal sheet inside of the "future microneedle" tube at subelement billet assembling will result in cladding of the microneedle inside diameter ID. Introducing metal sheet outside of "future microneedle" tube at subelement billet assembling will result in cladding of microneedles outside diameter OD. Cladding could be done with noble metal, platinum for example, or any suitable metal if necessary.

Figure 6B:
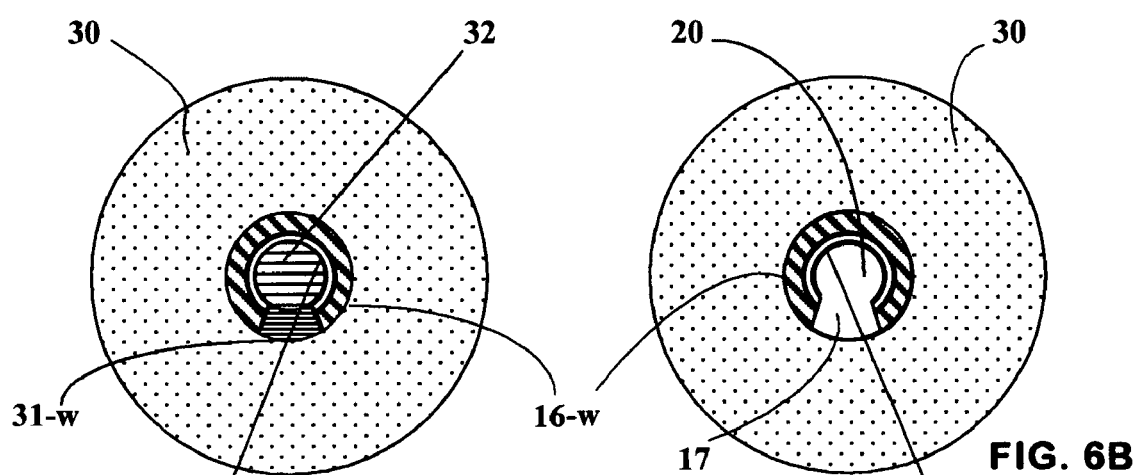
Figure 6C:
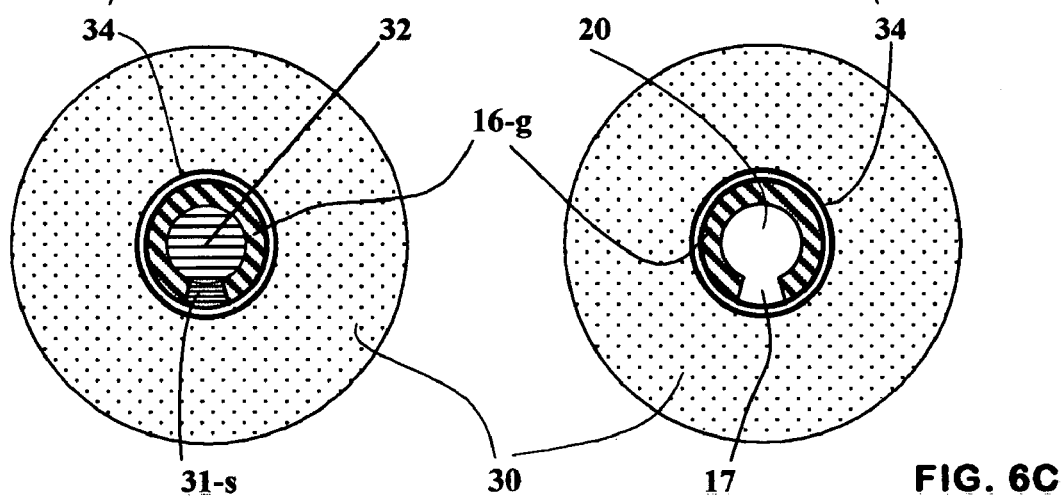

The FIG. 6B shows schematic of platinum 34 cladding on the ID of microneedle 16-*w*, and the FIG. 6C shows schematic of platinum cladding on the OD of microneedle 16-*g*.

The method is particularly useful to clad complex shapes, deep grooves and IDs. It is also useful for partial cladding. For example, one side of flat needle has a clad coating and other doesn't.

The FIG. 6C is example to demonstrate the capabilities of the process; it shows microneedle OD clad over gap 17. Etching a matrix and the needle core will form hollow needle 16-*g* having a thin layer or membrane of platinum covering over gap 17. A thin layer of noble metal would be one of many options available. It could be a layer (or several layers) of specified thickness of metal (or metals) a device manufacturer needs. Obviously the needle tube could be made of two different materials in concentric, or off-center (eccentric) geometry, and equal or variable thickness. This simple case also demonstrates combinations of concentric (barrier) and longitudinal (axial gap) geometry.

Billet Assembling:

Each gun-drilled hole is filled with one or several sub-elements, or the billet can is filled with a bundle of hex-shaped subelements and spacers (FIG. 5A). All billet components have to be cleaned and deep acid etched. Furthermore, any billet made of materials, which could be damaged by being exposed to air at elevated temperature (temperature of extrusion) has to be sealed inside of a can.

The billet ends are capped with plates (called 'nose' and 'lid') usually made from the same material as a billet.

Billets are evacuated to high vacuum ($10^4$ mm of mercury or better) and welded.

Finally the billets are preheated and hot extruded.

Suggested extrusion vendor: CSM Inc., of Coldwater, MI having 5500-ton press capacity. CSM extrudes most superconductors manufactured in US.

Mechanical properties of matrix and needle materials at elevated temperature are major factors to establish temperature of preheat and temperature of extrusion. Manufacturer of alloy always has to be able to provide the elevated temperature database. The extrusion vendor and material manufacturer are usually quite cooperative helping to establish extrusion parameters.

In extrusion process (see FIG. 4) the billet 23 positioned in a liner 54 is pushed with a ram 56 through a conical die 50. Creating the extrudate rod having diameter 52. Extrusion ratio R equals the area of billet cross-section divided by the area of cross section of the extrudate. R is usually between 10 and 40. After extrusion composite rod is drawn to final size, utilizing standard rod and wire drawing equipment. At final size composite rod has to be straightened and cut to length (2 meters, for example) convenient to handle on rod slicing machine. At final size a jacket, which protects composite at extrusion is very thin (~120 microns) and could be easily etched off.

Superconductor manufacturing is a relatively small industry; nevertheless the industry has sizeable surplus capacities developed in late 1980's in expectations for manufacturing large amount of very complex superconductor (filament diameter ~6 microns, filament number ~6500) needed for later abandoned Superconducting Supercollider. There are number of domestic and foreign manufacturers available to fabricate microstructural components composite.

Superconductors have to be made with high purity copper matrix and Nb, and Nb-46.5% Ti alloy filaments. This group has no matching of properties at elevated temperature and very poor matching of properties at room temperature. Materials restrictions frequently make manufacturing of superconductors very complicated. Superconductors manufacturers will be pleased to diversify and to have opportunity to fabricate composites made with materials having good property matching.

Fabrication of Metal Matrix Composite Slices

Metal matrix composite rod could be sliced employing all techniques and equipment available in the art of metalworking. Slices could be tumbled to cut edges and lapped if necessary.

Slice thickness equals microneedle length plus base thickness. The practical slice thickness range: 300–450 microns. Cutting shall not deform or damage tips of the future microneedles and microparts ends. For example, a metallographic sample saw (inexpensive and readily available equipment) produces excellent results. Cutting with a thin aluminum oxide wheel, applying low pressure, produce very good results also. Very light etching, just few microns, would remove all cutting imperfections. Increase speed and pressure at cutting and then remove imperfections by simple and fast etch could reduce cutting cost.

Vendor example: Metal Cutting Corporation of Cedar Grove, N.J. 07009. The Company (web site www.metalcutting.com) has completely automated equipment capable to cut thin slices of acceptable quality and reasonable cost. They offer tumbling and lapping also.

Etching of Metal Matrix Composite.

The components of microneedle slice (micropins, microparts assembly slice, etc.) 12: matrix 30, microneedles 16 and microneedles cores 32, see FIG. 7A, has to be selected as a group in such way that matrix and needles cores could be etched out without any damage to the microneedles. If non-etching barrier 45 (FIGS. 10A and B) is employed the etching shall not damage barrier also. Fortunately there are large number of metals and alloys available to assemble group of materials to meet those demands.

Example of such group: Ti—matrix, Nb—needles, Cu—needle core, Nb—non-etching barrier. Copper needle core could be etched out with nitric acid without damage to needles, matrix and non-etching barrier. Ti matrix could be etched with hydrofluoric acid without damage to needles or needles cores and non etch barrier. The matrix is etched down to expose the microneedles and to form microneedle base 18, (FIGS. 7A, B, C, D and E).

One more example. 304 Stainless steel—matrix, Ti—needles, Cu—needle core, Nb—non-etching barrier. Copper needle core could be leached out with nitric acid without damage to needles, matrix, and non etch barrier. Stainless steel matrix could be etched down with ferric chloride without damage to needles and non etch barrier. Ferric chloride will etch copper core, which is perfectly acceptable in this case.

Noble metal cladding would be acceptable for both groups.

Copper or low carbon steel as a chosen material for a can or jacket protecting composite billet from oxidation at extrusion would be acceptable for the both groups also. In case of stainless steel matrix, the jacket needed only if niobium non-etching barrier is utilized.

The polypropylene microneedles housing would be acceptable for the both groups.

Example of group for micropin or micropunch disk: steel—matrix, stainless steel—micropins. Etching reagent—copper nitrite mixed with nitric acid.

Examples of matrix materials: stainless steels, carbon steels, tool steels, alloyed steels, titanium and its alloys, copper alloys, silver and its alloys, nickel and its alloys, and noble metals and alloys.

In the case of the hollow microneedles, material of the core has to be different from materials of a corresponding matrix and microneedles to such extent that selected etching, dissolving, leaching, microblasting or combination of those means could remove the core without destroying or damaging of the matrix and microneedles.

Examples of materials for microneedles core: copper and copper alloys, silver and silver alloys, zinc alloys, iron and its alloys, steels, and titanium and its alloys.

In a case when materials exposed to high temperature at processing (like extrusion, hot compaction or sintering and high temperature anneals) selected materials should not poison, inter-diffuse, dissolve or damage each other. For example, very thin low carbon steel sheet has to be placed between Pt and copper to prevent copper to dissolve Pt at elevated temperature of extrusion.

For each case all selected materials, which are subjected to co-extrusion and co-drawing, has to have mechanical properties matching to extent that extrusion and/or drawing does not destroy the composite in process. For example, brittle alloys, like high-tin bronzes, would break in process. Another example, pure copper matrix will cause severe breakage of small titanium needles.

Examples of materials for microneedles: stainless steels, carbon steels, tool steels, alloyed steels, niobium and its alloys, titanium and its alloys, tantalum and its alloys, nickel and its alloys, noble metals and alloys, and binary and ternary combinations of thereof. Furthermore, a microneedle could be made with several materials, for example, main part of microtube made of niobium but a section of that tube is made of copper or titanium.

Examples of materials for microneedles cladding: noble metals and alloys particularly—platinum and its alloys, gold and its alloys, silver and its alloys, palladium and its alloys, and binary and ternary combinations of thereof. Niobium, tantalum, titanium, nickel, and vanadium are also good candidates for cladding.

Examples of materials for non-etching barrier. Nb, Ta, and noble metals.

The microneedle housing materials has to resist any of selected chemical(s) or erosion agents chosen for microneedles fabrication. The housing material examples: polypropylene, Teflon, polyethylene, PVC, epoxies, titanium and its alloys, copper and its alloys, stainless steels, and steels. For example, the micropunch as a tool should have the housing made out of stainless steel and that housing could be a part of the die assembly.

The Intermediate Stage of Etching.

Figure 7C:
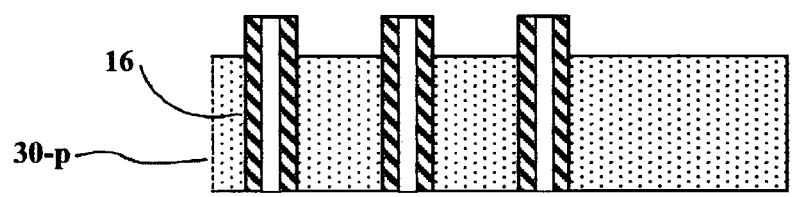
Figure 7D:
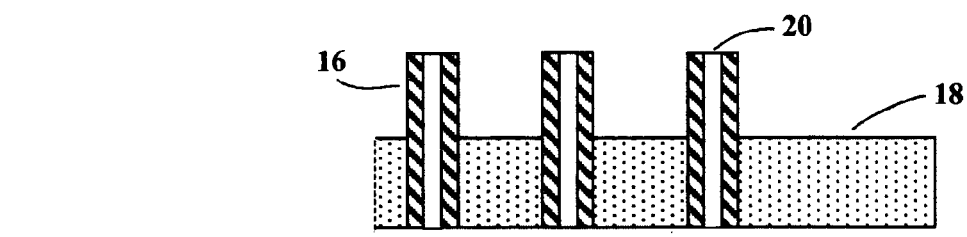
Figure 7E:
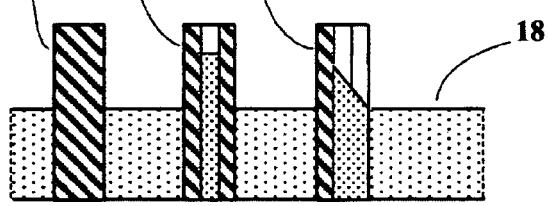

The matrix is partially removed and microneedles 16 are exposed to a fraction of its height over heavy base 30-*p*, see FIG. 7C. The exposed microneedles tips could be etched with different reagent by moving the whole load into next tank according to the chosen etching scheme.

At the intermediate stage of etching microneedles are short (height comparable to thickness) and very stiff. Whole slice at this stage is extremely rugged and would be able to withstand substantial forces associated with microblasting, micro particle erosion, severe agitation and handling. Because very little material removed at this stage of etching—micron or maximum few microns, needles tips etching could be done with reagents dissolving both needles and matrix.

At this stage, if desired, etching could change diameter of exposed part of the needle.

Microblasting is applying forceful and strong agitation of liquid or gas with suspended micro particles (0.05 μm aluminum oxide, for example) by pumping, spraying, air jets, vibration, ultrasonic or combination of them. The etching, and chemical polishing could be applied at this stage also. If microneedle cross-section has variation in thickness of elements (for example, microneedle tube wall has one side thinner then other)—thinner part will be reduced down faster than thicker one, thus changing shape of the microneedle tip. The double component wall needle with inner section harder than outer section will "self sharpen" in controlled way by microparticle erosion, microblasting or chemical polishing due to non-uniformity of such erosion ("rabbit tooth effect"). Similar sharpening will occur if central core of solid needle has greater wear resistance than outer. See FIG. 7A, assuming instead of copper core (needed to form a hollow shaft) titanium alloy is chosen in case of titanium microneedles, for example; that Ti alloy core will form a solid needle tip.

Height of microneedles can be controlled by controlling time duration in the bath. Tanks equipped with agitation and temperature control are needed for that type of simple etching. Reagents concentration control has to be implemented also. Etching of copper cores has to be done as a separate operation. Speed of core removal will depend on acid concentration and temperature. This process is well established and was used in the past. In 1960's millions hypodermic needles were manufactured by co-drawing stainless steel seamless tube with copper core and then etching the core out with nitric acid. Copper cores were etched out of needles up to 100 mm long. Compared to that, etching copper out of 300–400 microns long needles does not look like a big challenge.

A microneedle housing 41, is a thin plastic rim or enclosure, which frames the microneedle wafer like a picture frame, see FIG. 9B and FIG. 10B. Having the microneedles wafer embedded inside of a housing create option to separate microneedle manufacturing from a medical device fabrication. The housing with a wafer—assembly 40 (FIG. 9B and FIG. 10B) could be easily attached to a medical device.

Having slice 12 (FIG. 9A and FIG. 10A) embedded into the housing 41 (assembly 39) will make batch etching, which forms the needles, convenient and simple. Plus it will facilitate microneedles handling, assembling, transportation and storage. Leaching out the microneedles cores can be done either before or after of etching of a matrix.

Design in FIGS. 10A and B employs non-etching barrier 45. Acid has tendency to penetrate between plastic housing and microneedle wafer if it does not have non-etching barrier. Nevertheless there are many other ways to fabricate a non-etching barrier, for example, by employing anodizing, enamel coating, acid resistant paint, etc.

Protection for fabricating the one-sided assembly. Naturally, if one side is not protected from etching, microprotrusions will appear on both sides of the wafer. In order to produce one-sided part, for example, slices could be positioned on a tray lined up with an acid resistant adhesive tape or have a peel-off backing 43 attached to housing 41 (FIGS. 9A and B).

Examples of Microneedles and Microprotrusions Devices—the FIGS. 8A, B, C and D.

The FIG. 8A shows a microneedle syringe attachment 35 as a simple fixture utilized with a regular syringe 38. Microneedle housing assembly 40 is attached to a hub 36.

The FIG. 8B shows a simple microneedle patch 42 having a drug reservoir 44, microneedle housing assembly 40 is attached to the drug reservoir.

FIG. 8C—is side cross-sectional view of a section of an orthopedic implant assembly 46 having a microprotrusion surface array disk or insert 15-*s*. The disk is attached (press-fit and/or glued, for example) to an orthopedic implant (artificial bone) 48. In this example, the orthopedic implant could serve as a microprotrusion array insert housing. First a metal matrix composite slice has to be fitted in the "bone" and shaped to follow the bone contours if necessary, next step—developing microprotrusions by etching. The substrate of microprotrusion surface array disk could have controlled porosity also. Obviously, to assure adequate strength, thickness of the substrate (1 to 10 mm, for example) of the orthopedic microprotrusion surface array insert has to be much greater than thickness of drug delivery device microneedles substrate. In light of that the gun-drilled billet rout is not strictly necessary for implant fabrication.

The FIG. 8D—shows simple micropunch or micropin array disk 15-p being attached to a tool-holding rod 37. The housing, in this example, could be stainless steel tube (not shown).

Microneedle housing assembly 40 or its equivalent is a key component of drug delivery device. Obviously drug delivery device always could be designed to have microneedle housing assembly as an independent part connected later to the body of the device. Nevertheless, for example, syringe microneedles holder hub 36 (FIG. 8A) or microneedles patch 42 (FIG. 8B) could be designed to function as a microneedle housing thus eliminating need for detachable microneedle housing assembly.

CONCLUSIONS

A method of fabricating microstructural components is disclosed. More precisely, the method is for fabricating microparts and microparts assemblies. Partial removal of matrix will produce microparts assemblies having microprotrusions protruding from a substrate. Complete removal of a matrix will form microparts. Microneedles and micropunches are examples of microparts assemblies.

The method allows production of round or special shape needles, protrusions, pins, micropunches, microneedles etc. Microneedles are solid or hollow, similar to standard hypodermic needles, only on a much finer scale, arrayed with dozens, hundreds, or even thousands of other microneedles on a single base or substrate. The size, shape, number, and location of each individual microneedle in the array can be carefully controlled based on specific drug requirements or can be standardized for general application.

The microfabrication method includes: fabricating of unidirectional elongated metal matrix composite, cutting thin transverse slices of the composite, etching the matrix and forming microneedles. Etching out microneedles cores will form hollow microneedles. The process has no limitations for microneedle diameter (including nanoscale), height, aspect ratio (ratio between needle height and needle diameter), shape and distance between elements. The individual needle may includes several different materials in its making. The process also allows fabrication of microneedle base or substrate with controlled porosity and several different materials in its making. Furthermore, the method allows cladding microneedles with noble metal, and cladding whole composite rod with a barrier (the non-etching barrier of microneedles wafer is an example). Microneedles may have wide variety of axial gaps, which are expected to prevent tissues occlusion from blocking fluid flow.

Microneedles may be mounted into a microneedle housing. The final product is a microneedles wafer mounted into a housing, which is a component or a part of a medical microneedles device. The process is free from handling or assembling of micro-parts and separates microneedles manufacturing from a medical device fabrication. The microneedles housing facilitates convenient handling, assembling, storage and transportation. The process allows supplying the microneedles as readily available and inexpensive medical device component.

For each case selected matrix materials have to have chemical, physical and mechanical properties to be different from properties of microneedles to such extent that matrix could be removed without damage to microneedles. Final use will always be the most important criteria. For example, if strength is the property the user is looking for, steel matrix and stainless steel micropins (micropunches) would be preferable choice.

Metal Matrix Composites and Low Temperature Superconductors fabrication technologies evolved and matured in the last forty years. The current highly developed state of the art is result of considerable investments and work of generations of engineers and scientists. The technology is available to produce items and objects, which can be produced by other methods with great difficulty and expense, or not at all. In particular, the method is for fabricating microstructural components, microparts and microparts assemblies or arrays; nevertheless, the method could be utilized for manufacturing small parts, small parts assemblies, and arrays of small parts.

Partial removal of matrix will produce wide assortment of microparts assemblies. Microneedles wafer and micropunch disk are examples of the microparts assembly. Etching out only cores will produce micro-orifices. Etching a matrix entirely off will produce wide assortment of "individual microparts". For example, if matrix of the microneedle wafer is completely etched out we will have handful (from few to thousands) of small diameter tubes. In case of rectangular microneedles, it will be plurality of very small rectangular tubes. The thickness of a slice and depths of etching will define the length of tubes or shapes. The "individual micropart" could be of substantial complexity. Furthermore, it is not just complexity of shape; it also includes complexity of different materials metallurgicaly bonded together on microscopic scale. Another aspect of this method—it produces parts (microparts, microprotrusions, needles, microneedles, micropins, micropunches, microtubes, etc.) and micropart assemblies of high strength, as well as a high strength matrix and high strength bond (always metallurgical bond) between elements.

All components of a metal matrix composite made by extrusion and drawing always have favorable texture in longitudinal direction. As a result microneedles are of high strength yet ductile enough to be bent repeatedly without breaking. The method allows substantial control of a microstructure of the incoming components as well as a microstructure of components at intermediate stages of processing. Microneedles high strength is mainly result of the cold work applied to specific microstructures. The cold work texture, specifically the texture developed in direction of drawing, or longitudinal direction, together with control of microstructure of components produces the strongest man-made materials known, piano wire, for example. The method allows use of aging alloys to further increase strength of components.

Covering micropins tips with very hard materials like TiN (titanium nitride) or artificial diamonds is also feasible.

The metal matrix composite precursors offer the greatest control and flexibility in fabrication of microstructural components and are chosen as the main embodiment. Nevertheless, it is obvious that any unidirectional composite, natural or man-made, could be utilized to fabricate micro structural components and micro structural surfaces having microprotrusions. For example, polymer matrix composites, two phase-alloys having longitudinal texture, multi-phase alloys having longitudinal texture, and copper-niobium 'in-situ' high strength composite.

Although the description above contains many specificities, these should not be construed as limiting the scope of the invention but as merely providing illustrations of some of the embodiments and ramifications of this invention. Apparently widely different embodiments and ramifications of the present invention may be made without departing from the spirit and scope thereon.

I claim:

1. A method for fabricating microparts comprising the steps of:
   (A) fabricating a unidirectional metal matrix composite rod of predetermined dimensions and shape comprising of: (a) a matrix made of a first material and (b) at least one longitudinal element of predetermined dimensions and shape within said matrix made of a second material, (c) structure of said metal matrix composite is defined by plurality of said longitudinal elements spaced apart by surrounding said matrix material in substantially parallel arrangement, (d) said first or matrix material has to be selected to be different from said second or longitudinal elements material to such extent that said difference will allow removing of said matrix by a chemical reagent to the reaction of which said longitudinal elements are essentially chemically inert;
   (B) cutting said metal matrix composite in transverse direction, whereby forming sections of predetermined length;
   (C) utilizing said chemical reagent removing of said matrix from said sections completely, whereby forming at least one micropart of predetermined dimensions and shape, length of said microparts is equal to the length of said metal matrix composite sections wherein, said longitudinal elements having at least one core made of a third material, said third material has to be selected to be different from said longitudinal elements material to such extent that said difference will allow removing of said cores by said chemical reagent to the reaction of which said longitudinal elements are essential chemically inert;
   (D) utilizing said chemical reagent removing said core material and said matrix material from said sections completely, whereby forming at least one hollow micropart of predetermined dimensions and shape, wherein length of said hollow microparts is equal to the length of said metal matrix composite sections.

2. A method of fabricating hollow microneedles or hollow microprotrusions, comprising the steps of:
   (A) fabricating a unidirectional metal matrix composite rod of predetermined dimensions and shape comprising of: (a) a matrix made of a first material and (b) at least one longitudinal element within said matrix made of a second material, (c) said longitudinal elements are having cores made of a third material, (d) structure of said metal matrix composite rod is defined by plurality of said longitudinal elements spaced apart by surrounding said matrix material in substantially parallel arrangement, (e) said first or matrix material has to be selected to be different from said second or longitudinal elements material to such extent that said difference will allow removing of said matrix by a first chemical reagent to the reaction of which said longitudinal elements are essentially chemically inert, (f) said third or core material has to be selected to be different from said second or longitudinal elements material and the first or said matrix material to such extent that said difference will allow removing of said cores by a second chemical reagent to the reaction of which said longitudinal elements and said matrix are essentially chemically inert;
   (B) cutting said metal matrix composite rod in transverse direction, whereby forming slices of predetermined thickness;
   (C) utilizing said second chemical reagent removing said third or core material completely, whereby forming hollow shafts inside of said longitudinal elements;
   (D) utilizing said first chemical reagent partial removing, preferably from the one side of said slices, a substantially planar layer of predetermined thickness of said matrix, whereby forming a substantially planar substrate or a base having an array of hollow microprotrusions or hollow microneedles protruding from and attached to said substrate, length of said microneedles is equal to the thickness of said matrix layer removed.

3. The method of claim 2 further including:
   fitting of said metal matrix composite slices into a housing prior to etching, (a) said housing is chemically inert to any chemical reagents utilized in the process, whereby (b) said housing facilitates handling and protects said microneedles being processed and (c) said housing also facilitates assembling of said microneedles with a device.

4. The method of claim 2 wherein said substrate or base having thickness range within 0.2 to 2 millimeters.

5. The method of claim 2 wherein said hollow microprotrusions or hollow microneedles having diameter range within 30 to 200 microns.

6. The method of claim 2 wherein said hollow microprotrusions or hollow microneedles having length range within 150 to 3000 microns.

7. The method of claim 2 wherein said metal matrix composite rod is made by
   (a) extrusion of a billet having predetermined diameter and length, (b) said billet having at least one hole, (c) each said hole having at least one subelement rod inside, (d) each said subelement rod having at least one longitudinal element or a subelement-core.

8. The method of claim 2 wherein said metal matrix composite rod is made by
   (a) extrusion of a billet having predetermined diameter and length, (b) said billet is a tube of predetermined diameter and length, (c) said billet is filled with plurality of subelement rods of predetermined shape and predetermined dimensions, (c) plurality of said subelement rods are packed into a substantially tight fit bundle and fill up said billet, (d) each said subelement rod having at least one longitudinal element or a subelement-core.

9. The method of claim 2 wherein said metal matrix composite rod having a non-etching barrier of predetermined thickness around said rod circumference, said non-etching barrier has to be made of material selected to resist any reagents utilized in removing the matrix and core materials.

10. A method of fabricating small metal parts comprising the steps of:
   (A) utilizing available state of the art in metalworking to fabricate a rod having scaled up cross section of predetermined shape essentially the same as a future part cross section but on substantially larger scale;
   (B) encasing at least one of said rods in a metal jacket forming a subelement billet having said rod as a core and said jacket as a matrix;
   (C) reducing said subelement billet to predetermined size and shape forming subelements, said subelements having said shaped rods as a subelement-core;

(D) assembling a second stage billet using at least one said subelement as a building block;
(E) reducing said second stage billet to predetermined size to form a metal matrix composite rod with structure defined by plurality of said subelement-cores spaced apart in predetermined order by surrounding said matrix material in substantially parallel arrangement;
(F) said matrix material has to be selected to be different from said shaped rods material to such extend that said difference will allow removing of said matrix by a chemical reagent to the reaction of which said shaped rods are essentially chemically inert;
(G) cutting said metal matrix composite rod in transverse direction, whereby forming sections of predetermined length;
(H) Utilizing said chemical reagent removing of said matrix from said sections completely, whereby forming plurality of small parts, length of said small parts is equal to the length of said sections.

11. The method of claim 10 further including:
(A) providing said shaped rods having at least one core of predetermined shape and dimensions made of material, which has to be selected to be different from said shaped rods material to such extent that said difference will allow removing of said cores by a chemical reagent to the reaction of which said shaped rods are essentially chemically inert;
(B) removing said core material completely, whereby forming hollow shafts inside of said shaped rods;
(C) removing of said matrix from said sections completely, whereby forming at least one hollow small metal part of predetermined dimensions and shape, length of said small parts is equal to the length of the metal matrix composite sections.

12. The method of claim 11 wherein said small parts having 0.5 to 500 microns cross-sectional dimensions and up to 50 millimeters in length.

13. The method of claim 11 wherein said small parts having 0.5 to 6 millimeters cross-sectional dimensions.

14. The method of claim 11 wherein said parts having 6 to 25 millimeters cross-sectional dimensions.

* * * * *